United States Patent [19] [11] 4,211,116
Pilat et al. [45] Jul. 8, 1980

[54] ASSEMBLY FOR AND METHOD OF SAMPLING PARTICLE-LADEN FLUIDS AND A CASCADE IMPACTOR USED THEREWITH

[75] Inventors: Michael J. Pilat; Edward B. Powell, Jr., both of Seattle; John F. Thielke, Richmond Beach, all of Wash.

[73] Assignee: Electric Power Research Institute, Inc., Palo Alto, Calif.

[21] Appl. No.: 917,645

[22] Filed: Jun. 21, 1978

[51] Int. Cl.² .......................................... G01N 15/02
[52] U.S. Cl. ........................... 73/421.5 A; 73/432 PS
[58] Field of Search .............. 73/28, 432 PS, 421.5 A, 73/425.6; 55/270, 446, 274

[56] References Cited

U.S. PATENT DOCUMENTS

| | | | |
|---|---|---|---|
| 3,001,914 | 9/1961 | Andersen | 73/28 |
| 3,693,457 | 9/1972 | Pilat | 73/432 PS |
| 3,795,135 | 3/1974 | Andersen | 73/28 |
| 3,938,366 | 4/1976 | Wertlake et al. | 73/28 |
| 3,953,182 | 4/1976 | Roth | 73/28 |

OTHER PUBLICATIONS

"Submicron Particle Sizing with UW Mark 4 Cascade Impactor", by M. J. Pilat, E. B. Powell & R. C. Carr, Paper 77-35.2 presented at APCA Annual Meeting, Toronto (Jun. 20-24, 1977).
"Submicron Particle Sampling with Cascade Impactor" by M. J. Pilat, Paper No. 73-284, presented at APCA Annual Meeting, Chicago, (Jun. 28, 1973).

Primary Examiner—Anthony V. Ciarlante
Attorney, Agent, or Firm—Flehr, Hohbach, Test

[57] ABSTRACT

An assembly for and method of sampling particle-laden fluids for particulate content and particle size distribution are disclosed herein and utilized at least one cascade impactor adapted to be placed within the fluid stream to be sampled. This impactor includes a number of spaced, successive particle collection stages provided for collecting particles diminishing in size from stage to stage and specifically designed to prevent the rate of low of the fluid stream from any one stage to the next downstream stage from reaching its critical flow rate. The pressure at these stages is individually monitored utilizing individual transducers located in close proximity to the impactor and a monitor remotely located relative to the impactor.

8 Claims, 9 Drawing Figures

FIG.—1

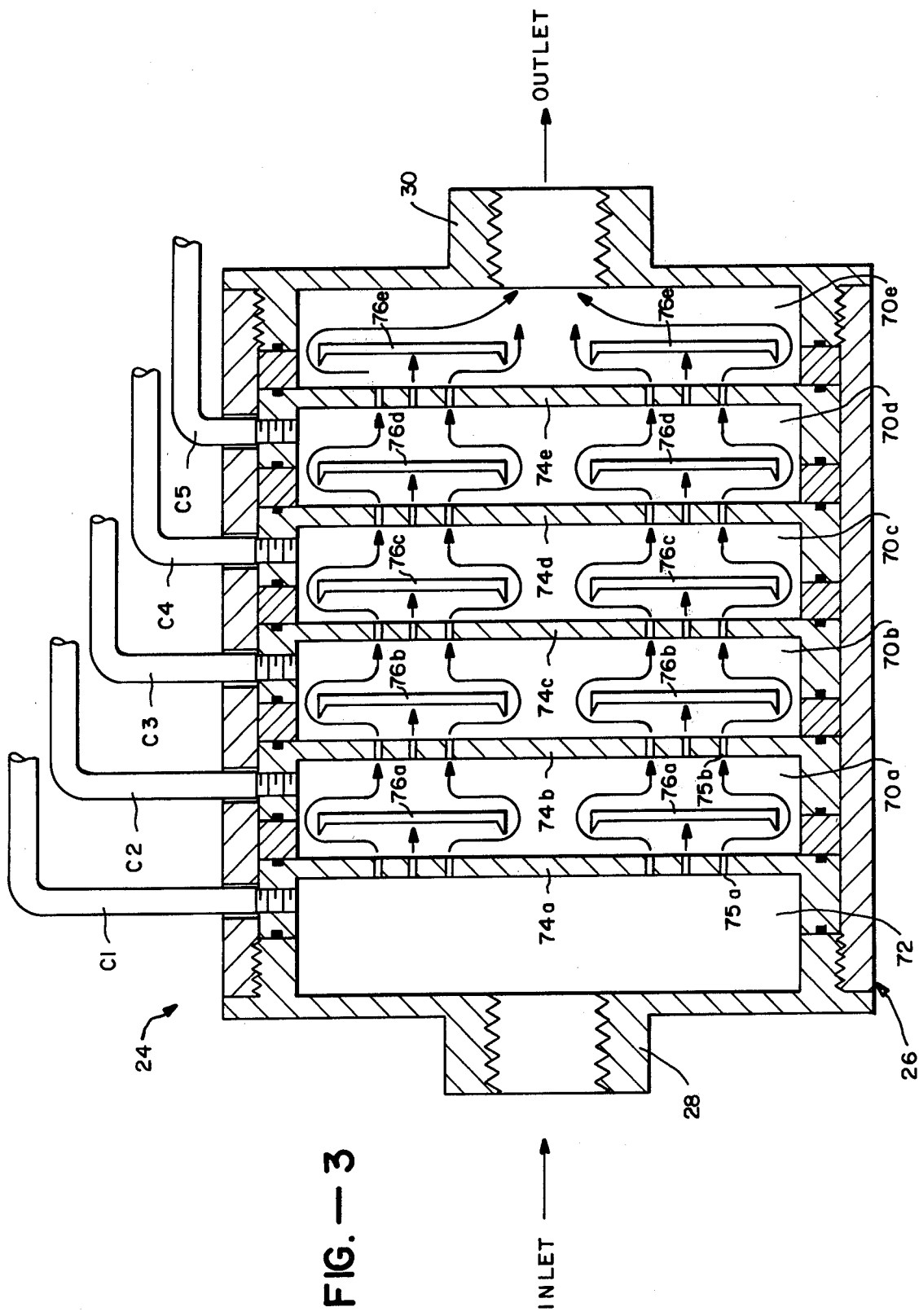
FIG.—3

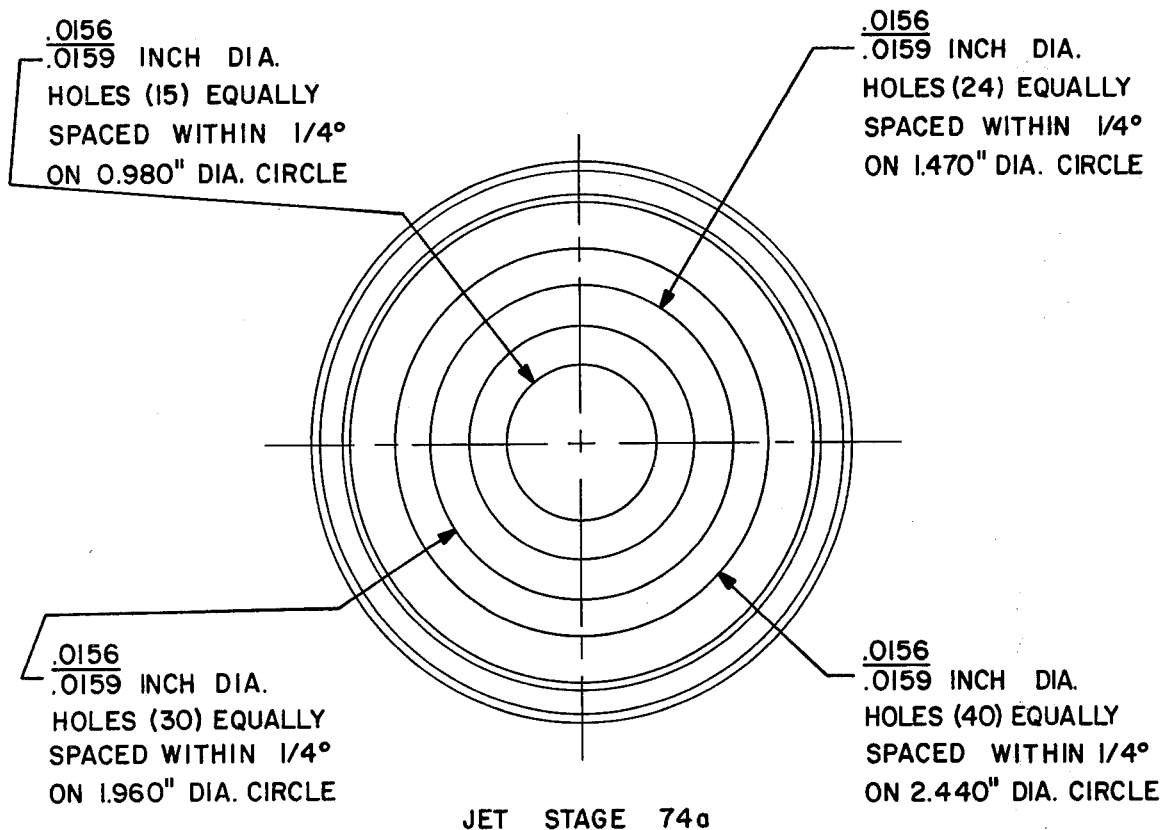
FIG.—4a
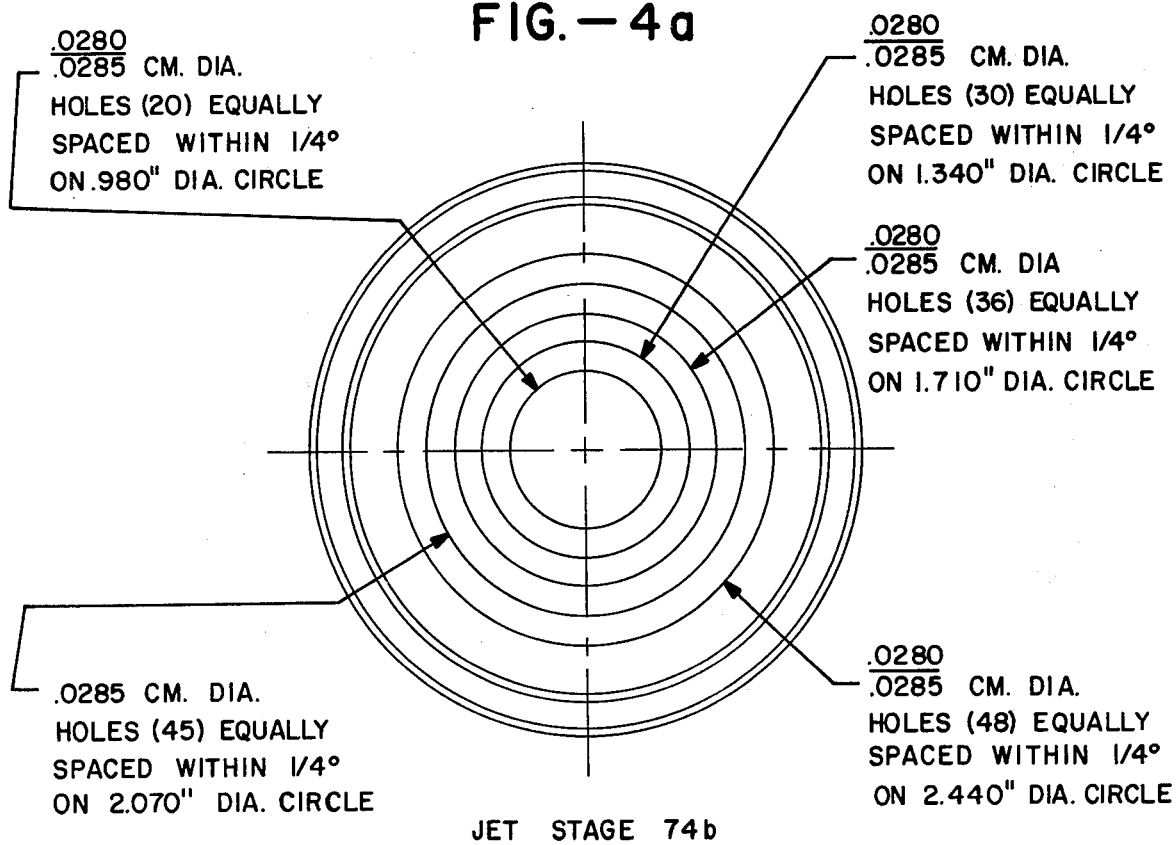
FIG.—4b

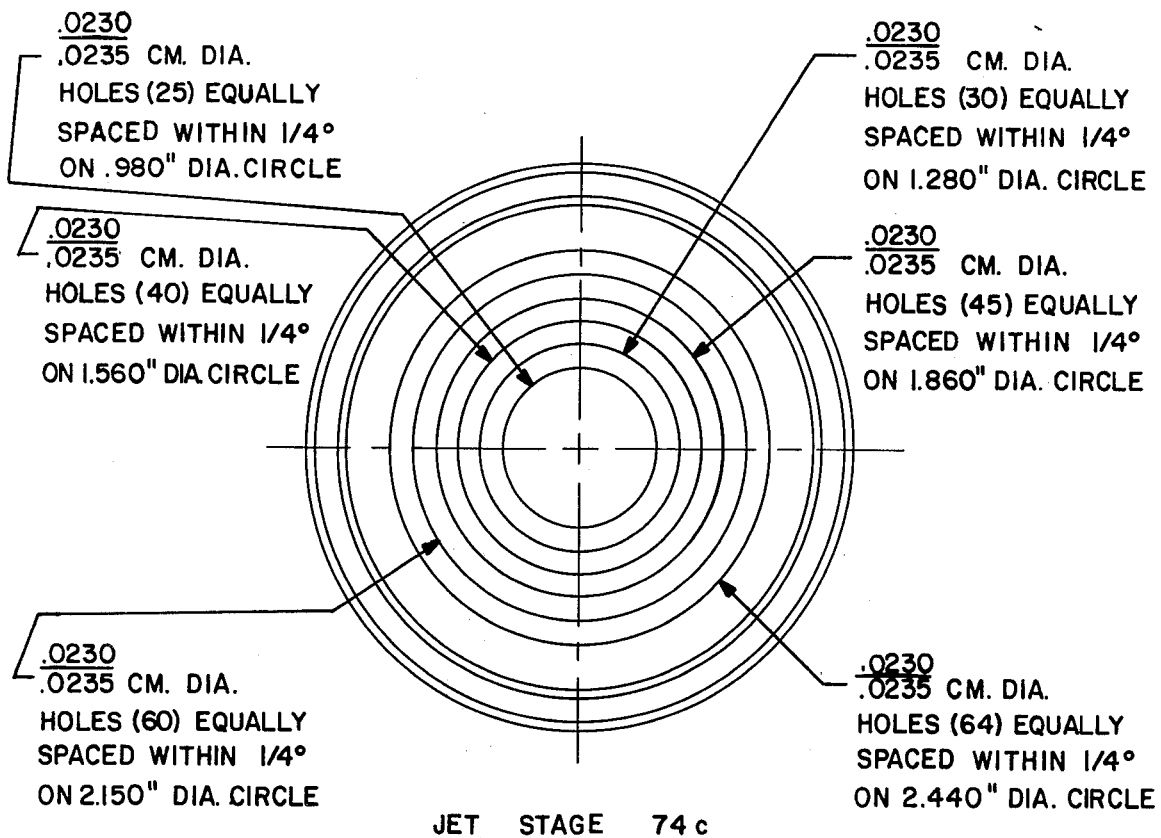
JET STAGE 74c
FIG.—4c
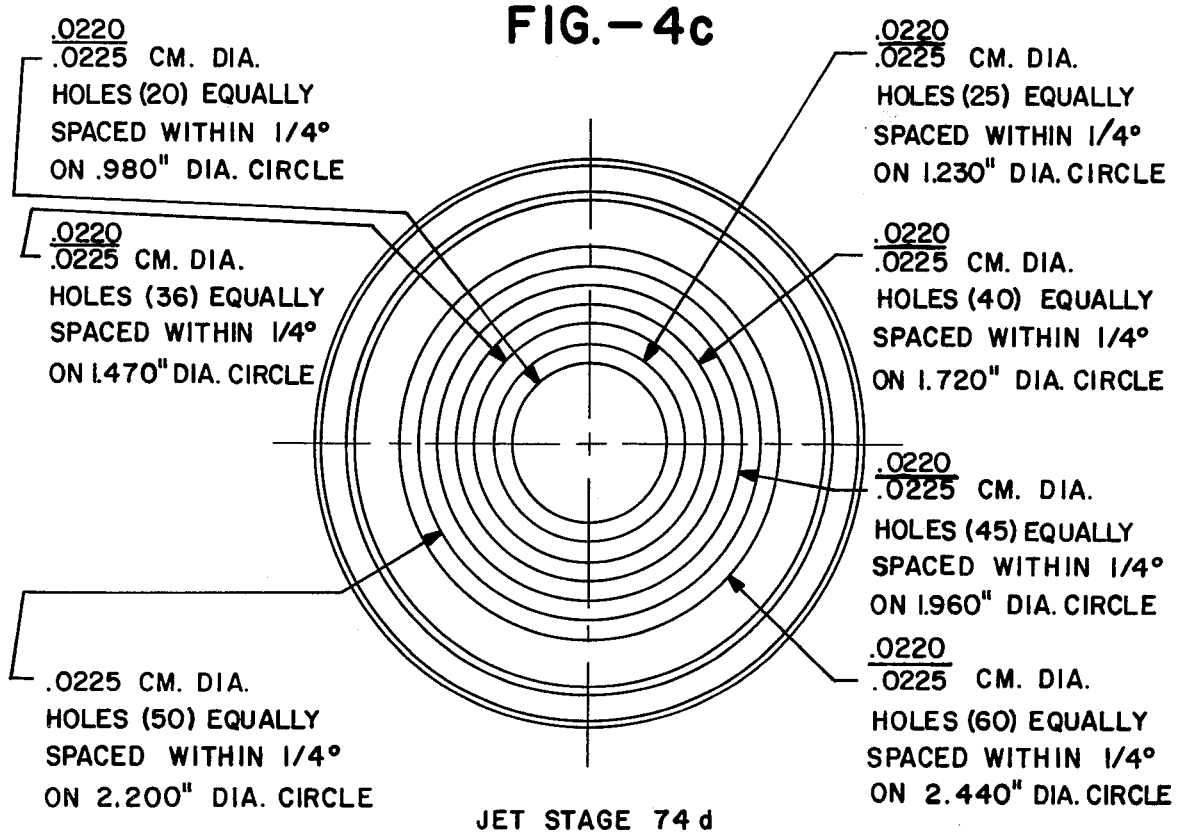
JET STAGE 74d
FIG.—4d

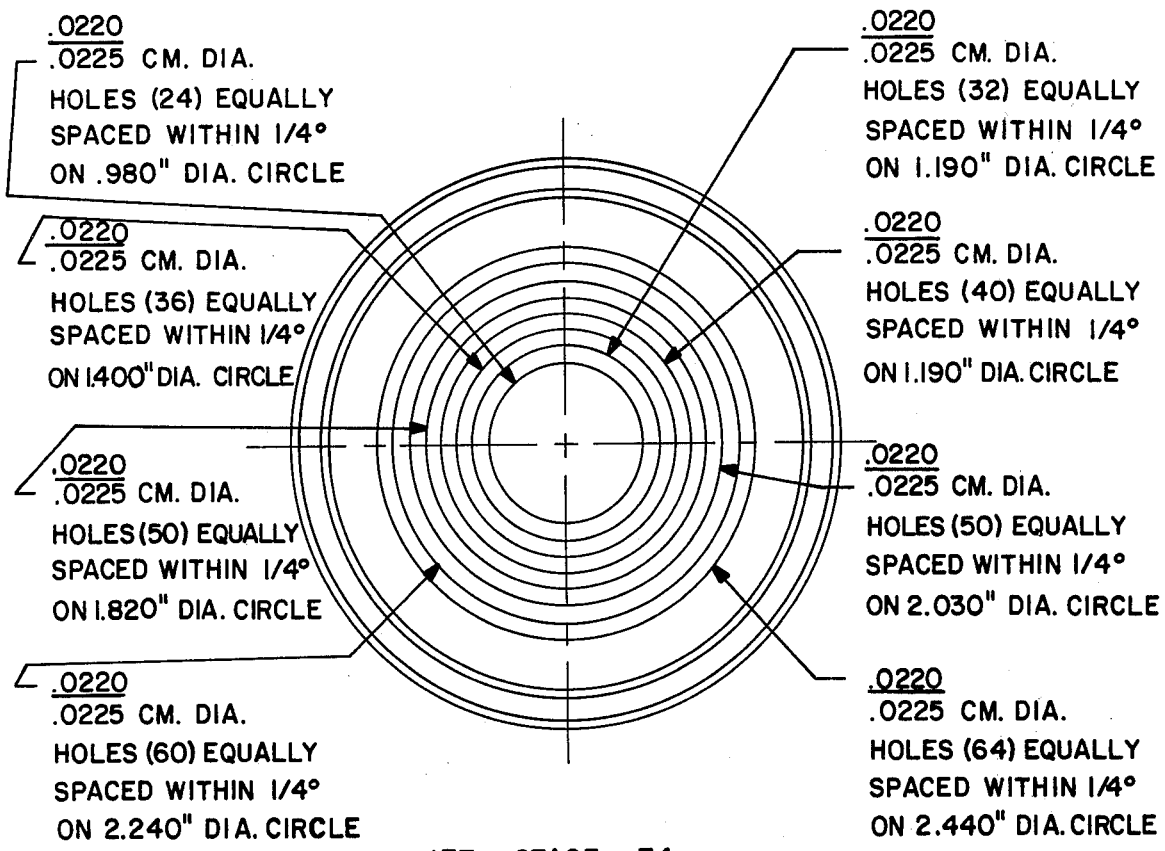
JET STAGE 74e
FIG. — 4e
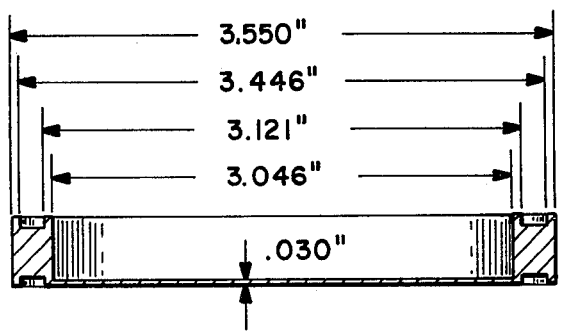
FIG. — 5

ASSEMBLY FOR AND METHOD OF SAMPLING PARTICLE-LADEN FLUIDS AND A CASCADE IMPACTOR USED THEREWITH

BACKGROUND OF THE INVENTION

The present invention relates generally to the sampling of particle-laden fluids for particulate content and particle size distribution and more particularly to a specific way of accomplishing this utilizing a cascade impactor having specifically designed collection stages.

As will be seen hereinafter, the overall particle sampling assembly provided in accordance with a preferred embodiment of the present invention utilizes a cascade impactor of the type disclosed in U.S. Pat. No. 3,693,457 which issued to M. J. Pilat on Sept. 26, 1972. This impactor, as disclosed in the patent, includes a longitudinally extending, tubular body having a fluid inlet and a fluid outlet and a plurality of longitudinally spaced, successive particle collection stages located within the tubular body between its inlet and outlet ends. In the cascade impactor, thus far described, the stream of fluid to be sampled, for example, the stream of particle-laden exhaust gases from a pool of coal burning steam generator or the like, is passed through apertured jet plates in successive collection stages where particles of diminishing sizes are respectively captured on collection plates respectively positioned in confronting relation with the jet plates, as discussed in more detail in the Pilat patent.

The cascade impactor just described comprises part of an overall assembly train including a filter at the outlet of the impactor as well as a dry gas meter including pressure gauges and a vacuum pump downstream therefrom. This assembly may also include a downstream condensor (not specifically illustrated in the Pilat patent) and impingers within a constant temperature bath (illustrated in the Pilat patent) located upstream of the dry gas meter for preventing moisture from entering the meter.

A more recent development in the overall assembly just described has been the addition of a second cascade impactor operatively positioned downstream of the impactor described, that is, between the outlet end of the first impactor and the downstream filter recited above. This second or downstream cascade impactor is similar to the impactor described above in that it includes a longitudinally extending, tubular body having an inlet and an outlet as well as a number of successive particle collection stages located within the tubular body between its inlet and outlet. However, the pressure across the successive stages of this latter impactor, rather than being relatively constant from its inlet to its outlet as in the cascade impactor described above, decreases in pressure from stage to stage which was briefly alluded to in the Pilat patent. The primary reason for providing pressure drops between successive particle collection stages in this second or downstream impactor is so that the latter is capable of collecting substantially smaller particles, for example, those in the submicron range, specifically those which are in the range of 0.2 microns in diameter.

In order to more fully understand the present invention, it is important to briefly discuss the theory behind the cascade impactors described herein, even though a similar discussion was provided in the Pilat patent. The cascade impactor thus far described, whether it is the initial upstream impactor or the second downstream impactor, fractionates the particulate matter within the particle-laden fluid stream into size increments by inertial impaction of the particles on a collection surface. This occurs at successive stages within the impactor and the resulting index of particle size is traditionally expressed by the particle size collected within 50% collection efficiency for each stage, typically referred to as the "$d_{50}$". The particle diameter has been related to the Stokes inertial impaction parameter $\Psi$ which is defined by Ranz and Wong (1952) as $$\psi = \frac{C\rho d_p^2 V_j}{18\mu D_j} \tag{1}$$

where C is the Cunningham correction factor, $\rho$ the particle density, $d_p$ the particle diameter, $V_j$ the gas velocity in the jet, $\mu$ the gas viscosity and $D_j$ the jet diameter. Solutions of the equation of particle motion at various magnitudes of $\Psi$ and experimental studies have shown that the Stokes inertial impaction parameter at 50% collection efficiency ($\Psi_{50}$) for a particular diameter ($d_{50}$) ranges between 0.12 and 0.17 for circular jets. These values were originally reported by Ranz and Wong (1952) and later confirmed by McFarland and Zeller (1963). Solving for the particle diameter from equation 1 gives $$d_{50} = \left[ \frac{18\mu D_j \psi}{C\rho_p V_j} \right]^{\frac{1}{2}} \tag{2}$$

Substituting an average value of 0.145 for $\Psi_{50}$ provides an equation for $d_{50}$, $$d_{50} = \left[ \frac{2.61\mu D_j}{C\rho_p V_J} \right]^{\frac{1}{2}} \tag{3}$$

Equation 3 provides an expression which relates the cascade impactor stage $d_{50}$ and the impactor parameters. These parameters can be appropriately altered to provide an even distribution of $d_{50}$'s throughout the impactor stages. For sizing of submicron particles, the Cunningham correction factor becomes of particular significance due to the physical limitations in further altering the other impactor parameters. The Cunningham correction factor C is defined by an equation reported by Davies (1945)

$$C = 1 + \frac{2\lambda}{d_{50}} [1.257 + 0.40 \exp(-1.10 \frac{d_{50}}{\lambda})] \tag{4}$$

where $\lambda$ is the gas mean free path. The relationship of the Cunningham correction factor to the absolute gas pressure for various particle diameters is illustrated in FIG. 1. Thus it can be seen by examination of equations 3 and 4 and FIG. 1 that it is possible to select the appropriate magnitudes of the impactor parameters necessary to provide a stage $d_{50}$ as low as 0.02 microns. Assuming a particle density $\pi$ of 1.0 gram/cm$^3$ and substituting into equation 3 provides an equation for the aerodynamic cut diameter $da_{50}$ $$da_{50} = \left[ \frac{26.1\mu D_j}{CV_j} \right]^{\frac{1}{2}} \quad (5)$$

In summarizing the foregoing with particular reference to equation 5, it should be quite apparent that the size ($da_{50}$) of particles collected at any given stage of the impactor is dependent on the diameter of the apertures through the jet plate in that stage (the jet diameter $D_j$), the viscosity of the fluid passing through the jet hole (the gas viscosity $\mu$), as well as the velocity of the fluid through the jet ($V_j$) and the Cunningham correction factor (C) as discussed above. Obviously, the gas viscosity is fixed and the jet diameter is fixed, thereby leaving only the Cunningham correction factor C which might vary (with pressure) and the jet velocity which is known to depend on the flow rate (a possible variable) through the apertures as well as the jet diameter (a constant) and the number of apertures (also a constant). Accordingly, in order to accurately monitor the $da_{50}$ at any given state, it is necessary to continuously monitor the Cunningham correction factor (a possible variable) and the jet velocity (another possible variable). In order to monitor the Cunningham correction factor, it is necessary to monitor the pressure at that stage which can be calibrated in terms of the Cunningham correction factor using the information in the graph of FIG. 1 and/or equation 4. While it is possible to monitor the velocity of gas through the various apertures in the jet plate, this would disrupt the jet stream through the impactor. However, since the number of apertures in the plate is known and their size, it is only necessary to monitor the overall flow rate through the impactor for converting this information to jet velocity through any given aperture plate.

In view of the foregoing, the overall particle sampling assembly including the cascade impactor of the type just described also includes an arrangement for monitoring the pressure at each collection stage thereof. This arrangement has heretofore included a plurality of gas tubes, one for each stage, extending from the various impactor stages to a remote location, specifically to a location where the operator maintains his control equipment. Typically, the operator would monitor the various stages, one at a time, utilizing some sort of conventional pressure gauge.

It should be quite apparent that the monitoring procedure just described is time-consuming and tedious. Moreover, it is quite possible for the operator to inaccurately record the pressure values which are successively taken from stage to stage, thereby resulting in an inaccurate Cunningham correction factor. In addition, because the cascade impactor may include a relatively large number of stages, for example, as many as 28, it necessarily includes an equal number of pressure sampling tubes leading from the impactor to the relatively remote control station. This not only adds cost to the overall assembly and is quite inconvenient, especially when the sampling procedure is carried out in relatively close quarters, but in some cases, the space requirements are not at all sufficiently flexible (regardless of convenience) to allow a large number of pressure sampling conduits to extend between the impactor and control station.

As will be seen hereinafter, the overall particle sampling assembly of the present invention does not monitor the various collection stages using a single pressure gauge, and it does not utilize relatively inflexible fluid carrying conduits extending between the impactor and control station. Rather, as will also be seen, the overall assembly of the present invention monitors the pressure at the various stages simultaneously and continuously throughout the assembly operation, utilizing transducers located at the impactor for converting the pressure at each stage to a corresponding electrical signal. These signals are carried back to the remote control station by flexible electrical cables which can readily adapt to the space requirements and which are relatively convenient for the operator. At the control station, these signals can be readily converted electronically to visual and/or permanent readouts (either stage-by-stage or simultaneous readouts) and they may be appropriately calibrated to readout in the form of the Cunningham correction factor without requiring conversion by the operator.

From the foregoing, the importance of accurately monitoring the Cunningham correction factor for accurately determining the $da_{50}$ at any given detection stage should be quite apparent. However, it is equally important to prevent the rate of flow of the fluid from one stage to the next (through successive jet plates) from reaching its Critical Flow Rate (CFR). Briefly stated, CFR is the rate at which the velocity of the fluid passing from one stage to the next downstream stage does not increase with a drop in pressure (within practical limits) from the upstream stage to the next downstream stage. In the past, this was accomplished by designing the various collection stages to have a mach number such that the jet stream through any specific aperture was subsonic. However, Applicants have discovered that this does not reliably prevent the rate of flow of the fluid stream from reaching its Critical Flow Rate. Accordingly, the Cunningham correction factor at one stage of the cascade impactor may be different than the Cunningham correction factor at the next stage while the jet velocity at each stage is the same (because the flow rate between the two has reached its CFR level). This, of course, ultimately leads to inaccuracies in the $da_{50}$ at the downstream collection plate since the velocity onto that plate is not truly what it should be based on its lower pressure (compared to the upstream stage).

As will be seen hereinafter, the cascade impactor constructed in accordance with the present invention is designed in a more reliable way to prevent the rate of flow of the fluid stream from one stage to the next from reaching CFR and thus assuring that the jet velocity for any particular aperture between these stages is truly indicative of the pressure drop across that stage. As will also be seen, this is accomplished by designing the apertures in any given gas jet plate to be below a predetermined ratio of pressure at its upstream side (within the upstream stage) as compared to the pressure on its downstream side (the pressure within the downstream stage). The ratio selected is one known in the art, specifically the Critical Pressure Ratio (CPR) below which the gas flows through the apertures at a rate below its CFR level. This ratio as will be discussed is a constant, specifically about 1.71.

OBJECTS AND SUMMARY OF THE INVENTION

One object of the present invention is to provide an overall particle sampling assembly (and method) of the general type described and particularly one which utilizes a cascade impactor capable of collecting particles in the submicron size range, specifically an impactor having successive collection stages which decrease in pressure from stage to stage.

Another object of the present invention is to monitor the pressure at the various stages in this lastmentioned cascade impactor using locally positioned transducers so as to provide electrically powered readouts thereby eliminating relatively inflexible pressure sampling conduits between the impactor and remotely located control stations.

A further object of the present invention is to provide a particular cascade impactor for use in the assembly recited above and particularly one which is designed to more reliably prevent the rate of flow of the fluid stream from any one stage to the next downstream stage from reaching its Critical Flow Rate.

Still a further object of the present invention is to specifically design the various stages within this lastmentioned cascade impactor such that the pressure ratio between any two adjacent upstream and downstream stages is below the Critical Pressure Ratio, that is, below 1.71.

In accordance with one aspect of the present invention, a particular way of sampling particle-laden fluids for particulate content and particle size distribution is disclosed herein and utilizes at least one cascade impactor adapted to be placed within the fluid stream to be sampled. This impactor includes a longitudinally extending tubular body having a fluid inlet and a fluid outlet and a plurality of longitudinally spaced, successive particle collection stages located within the tubular body between its inlet and its outlet and, together with this body, defining a fluid flow path from the inlet through successive particle collection stages to the outlet. As stated previously, these stages are constructed and positioned so as to produce successive drops in pressure from one stage to the next as the stream of fluid moves along its path from the inlet to the outlet.

One particular aspect of the present invention resides in the particular way in which all of the collection stages just recited are simultaneously monitored throughout the assembly operation. As will be seen hereinafter, this is specifically carried out by sampling the pressure at each stage and transducing each of these pressure samples to a corresponding electrical signal, at a location adjacent to that stage. These signals are carried to a remote location by means of flexible cables where they are used to indicate the pressures at the various stages.

Another aspect of the present invention resides in the utilization of a cascade impactor having particle collection stages designed to reflect more reliably the $da_{50}$ particles collected at any given stage by more reliably preventing the rate flow of the fluid stream from any one stage to the next downstream stage from reaching CFR. As stated previously, this is specifically accomplished by maintaining the pressure ratio between any given upstream stage and adjacent downstream stage below the Critical Pressure Ratio.

BRIEF DESCRIPTION OF THE DRAWINGS

FIG. 3 is a vertical sectional view of a cascade impactor designed in accordance with the present invention and comprising part of the overall assembly of FIG. 1.

FIGS. 4a-4e are plan views of jet plates used in an actual working embodiment of the impactor illustrated in FIG. 3.

FIG. 5 is a cross-section view illustrative of each of the jet plates shown in FIGS. 4a-4e.

DETAILED DESCRIPTION AND PREFERRED EMBODIMENTS

Figure 1:
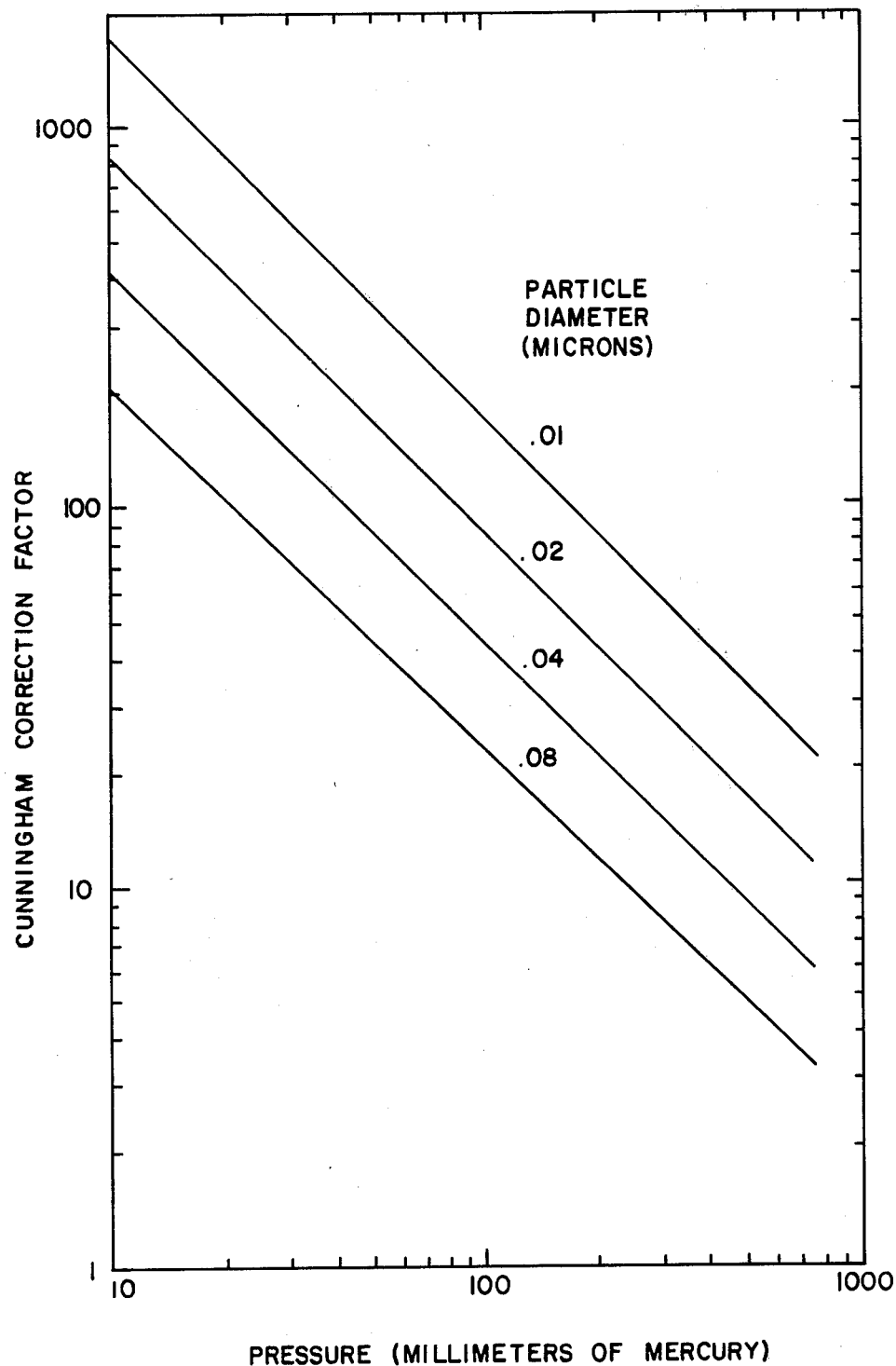
FIG. 1 is a graphic illustration of the Cunningham correction factor as it relates to pressure at a temperature of 70° F.
Figure 2:
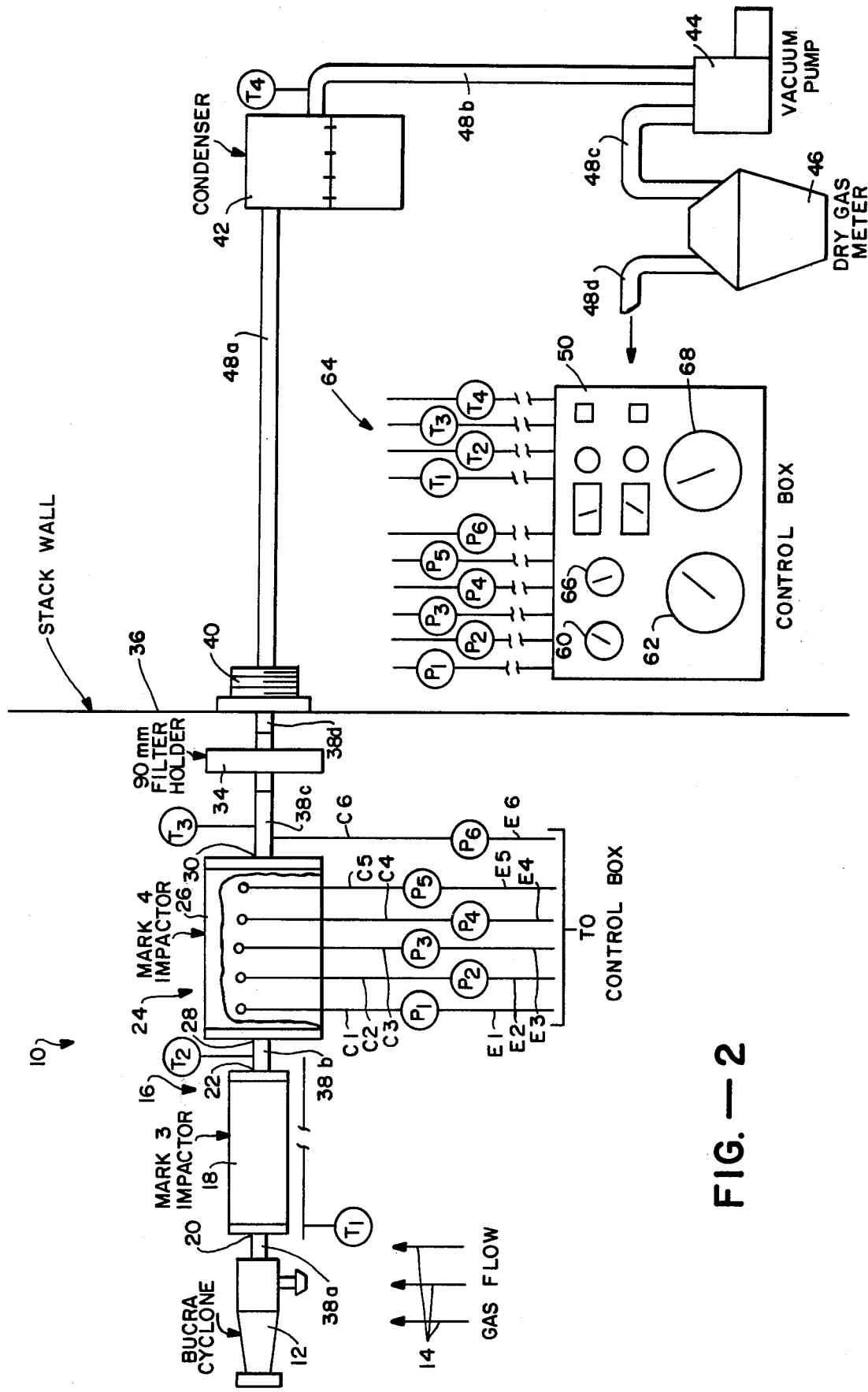
FIG. 2 is a schematic illustration of an overall particle sampling assembly designed in accordance with the present invention.

Turning now to the drawings, attention is specifically directed to FIG. 2 illustrating an assembly 10 which is designed in accordance with the present invention and which is provided for sampling particle-laden fluids for particulate content and particle size distribution. As will be seen below, this assembly operates generally in the same way as the overall sampling train described in the previously recited Pilat patent. Differences between the two will become apparent hereinafter.

As illustrated in FIG. 2, assembly 10 includes a BCURA (British Coal Utilization Research Association) cyclone 12 which is located at the downstream end of the assembly and which is adapted for insertion into the fluid stream being sampled, for example, into the exhaust gases of a coal powered steam generator or the like. This cyclone has the advantage of permitting continuous samples to be taken in a direction perpendicular to the gas stream which is generally indicated by the arrows 14, thereby eliminating the use of an awkward 90° probe.

Continuing down the stream of assembly 10, it can be seen that the latter includes a first or upstream cascade impactor generally designated at 16. Inasmuch as this impacter may be identical to the impacter described in the Pilat patent, it will not be discussed in detail herein, reference being made to the patent. It suffices to say that this cascade impacter includes a longitudinally extending, tubular body 18 having an inlet end 20 and an outlet end 22 as well as a plurality of longitudinally spaced, successive particle collection stages (not shown) located within tubular body 18 between its inlet end 20 and its outlet end 22. In an actual working embodiment, impacter 16 has seven stages in all and for purposes of calculating the $d_{50}$ at each stage (equation 3 or 5 recited previously), it is generally assumed that there is negligible pressure drop across the impacter and, hence, negligible pressure drop from stage to stage.

Assembly 10 includes a second cascade impacter which is generally designated at 24 and which is connected in line directly downstream from impacter 16 for collecting particles in the submicron range. Cascade impacter 24 will be discussed in detail hereinafter with respect to FIG. 3. For the moment, it suffices to say that this impacter, like cascade impacter 16, includes a longitudinally extending tubular body 26 having a fluid inlet 28 at one end and a fluid outlet 30 at the other end and a plurality of longitudinally spaced, successive particle collection stages (not shown in FIG. 2) which are located within the tubular body between its inlet and its outlet ends. However, unlike cascade impacter 16, the various successive collection stages within impacter 24 are specifically designed and positioned so as to cause carefully determined successive drops in pressure between the stages as the stream of fluid moves through body 26 from its inlet end to its outlet end. As stated previously, this increases the Cunningham correction factor from one stage to the next by successively decreasing the pressure at each stage. However, as also stated previously, this requires the pressure at each stage to be monitored, as will be discussed hereinafter.

The two cascade impacters 16 and 24 comprising part of assembly 10 only capture and collect a portion of the particles within the fluid stream being sampled. The remaining particles are captured and collected by a filter arrangement 32 connected directly downstream from the outlet end 30 of impacter 24. This filter arrangement includes a filter holder 34 which is preferably a 90 mm filter holder used to reduce the pressure drop across the filter. A filter (not shown) is located within the holder and in an actual embodiment is a type A/E Gelman glass fiber filter, sandwiched between two TEFLON (trademark) gaskets placed on a support screen.

As illustrated in FIG. 2, the various components of assembly 10 thus far described are all shown positioned within the stack including fluid stream 14, as generally indicated by a stack wall 36. These various internally located components which together may be referred to as an assembly probe may be maintained in the position illustrated by interconnecting tubular conduits 38a, 38b, 38c and 38d as well as a suitable lock nut arrangement 40 connected with conduit 38d and wall 36.

The remaining components making up the overall assembly illustrated, with the exception of a pressure monitoring arrangement and temperature monitoring arrangement (to be described), are all located outside of and remote from stack wall 36. These external components include a condenser 42 positioned directly downstream of filter 34, a vacuum pump 44 positioned downstream of the condenser and a dry gas meter 46 positioned downstream of the vacuum pump. The condenser which is interconnected for fluid communication with filter 34 by means of a flexible conduit 48a may be of any suitable type and in an actual working embodiment is a tubular, low pressure drop, coil design, built with three quarter inch copper tubing and housed in a fifteen gallon galvanized container. This condenser serves to eliminate moisture in the fluid stream before the latter reaches the vacuum pump. In the working embodiment, once the moisture is condensed, this condensed water is separated in a stainless steel impinger type water trap located at the base of the coil. The vacuum pump, which is interconnected in fluid communication to the condenser by means of flexible conduit 48b, may also be conventional. In an actual working embodiment, it is a two stage, rotary vane, leakless vacuum pump built by Alcatel Inc. (Model ZM2012) and is capable of maintaining an ultimate vacuum of $10^{-4}$ Torr and a free air flow of 10.6 cfm. The dry gas meter 46 which is interconnected in fluid communication with the vacuum pump by means of flexible conduit 48c is provided for measuring overall gas flow by means of a meter indicator and, like the vacuum pump, may be conventional. In an actual working embodiment, the dry gas meter is a Rockwell 175-S temperature compensating dry gas meter. As illustrated in FIG. 2, the gas through the meter may be exhausted to the ambient surroundings by means of flexible conduit 48d.

In addition to the various external components just described, assembly 10 includes another external component, specifically control box 50. This control box which is preferably located at an operator controlled station remote of the internal probe components, that is, remote from the stack wall, is provided for housing a number of conventional control components (which do not require a discussion) as well as portions of an overall pressure monitoring arrangement and temperature monitoring arrangement.

As stated previously, in order to calculate the $d_{50}$ at any given stage in the downstream impactor 24, it is necessary to monitor the pressure at that stage. This is accomplished by an overall pressure monitoring arrangement generally designated by the reference numeral 52. This arrangement includes a plurality of pressure sampling tubes C1, C2, C3 and so on, one for each collection stage within impactor 24. While each of these conduits is only shown diagrammatically in FIG. 2, it is to be understood that each is an actual conduit as illustrated in FIG. 3, preferably constructed of copper. As will be discussed with respect to FIG. 3, one end of each of these conduits is in fluid communication with its associated collection stage and, in accordance with one aspect of the present invention, its other end terminates in close proximity to the impactor as seen in FIG. 2. These outer ends, which are nevertheless located within the fluid stream stack, are connected to conventional transducers P1, P2, P3 and so on and each transducer is responsive to the continuous sampling of pressure from its associated conduit for transducing the pressure samples to a corresponding electrical signal at its output. The various electrical signals from transducers P1, to P6 are carried to the control box 50 by means of flexible lead wires E1 to E6. In this way, rigid pressure sampling conduits are only required in short straight lengths.

Pressure monitoring arrangement 52 also includes a conventional circuit including at least one visual indicator 60 located within control box 50 and connected with all of the transducers P1 to P6 by electrical conduits E1 to E6. This latter means is responsive to the electrical signals which are simultaneously provided at the outputs of the transducers during operation of the overall assembly for indicating the pressure at each of the stages during operation of the assembly. In this regard, this latter means may also include a collection stage selection dial 62 appropriately interconnected with indicator 60 and the various conduits E1 to E6 for individually monitoring the pressures at the various stages, as illustrated in FIG. 2. However, the overall monitoring arrangement could include a visual indicator for each stage so that all of these stages are simultaneously monitored. Moreover, this arrangement could include conventional permanent readout means (not shown). In addition, while in an actual working embodiment, the electrical signal converting means provides a visual indicator which is actually calibrated to indicate the pressure at the various stages, it could be readily calibrated to read out as the Cunningham correction factor without the necessity of further calculations by the operator.

In addition to pressure monitoring arrangement 52, assembly 10 may include a conventional temperature monitoring arrangement which is generally designated by the reference numeral 64. This arrangement in the embodiment illustrated includes four thermocouples generally designated at T1, T2, T3 and T4. Thermocouple T1 is positioned at the inlet end 20 of cascade impactor 16 for measuring the temperature of the fluid stream being sampled at that point. Thermocouple T2 is located at the interconnected outlet end 22 of impactor 16 and the inlet end 28 of impactor 26 for sensing the temperature of the stream there. Thermocouple T3 is located between the outlet end of this latter impactor and the inlet end of filter 32 for sensing the temperature there and thermocouple T4 is located at the outlet end of condenser 42 for sensing its temperature. While not shown, each thermocouple produces an electrical output signal which corresponds to the temperature being sensed and this signal is carried to the control box 50 by means of a suitable electrical lead wire. These lead wires are interconnected to conventional means which drive an indicator 66 for visually indicating the temperature at that point. As illustrated in FIG. 2, a single indicator is shown along with a manual selector 68 suitably interconnected to read out the various temperatures individually.

From the foregoing, it should be readily apparent that overall assembly 10 is capable of continuously monitoring the pressure at each stage of impactor 24 (using pressure monitoring arrangement 52) and is also capable of continuously monitoring the gas flow rate through the entire assembly and hence through the various stages in the cascade impactor 24 (by means of dry gas meter 46). Accordingly, it should be quite apparent that by appropriate calculations using the constant design criteria of the various stages (actually the jet plates within the stages, to be described with respect to FIG. 3), the Cunningham correction factor C and the jet velocity $V_j$ at each stage can be readily calculated and, therefore, the $d_{50}$ (or $da_{50}$) at each stage can be readily calculated. In this regard, as stated previously, it is quite important that the measured Cunningham correction factor C and jet velocity $V_j$ are accurately reflected by the pressure at the various stages. As will be seen hereinafter, cascade impactor 24 is specifically designed to accomplish this.

Turning to FIG. 3, attention is directed to cascade impacter 24. As seen in this figure, the impacter includes previously recited impacter body 26 having fluid inlet 28 and fluid outlet 30. As also stated, this impacter includes a plurality of longitudinally spaced, successive particle collection stages located within the tubular body between its inlet and outlet end. These successive stages, five in all in the embodiment illustrated, are generally illustrated by the reference numerals 70a, b, c and so on, from inlet end 28 to outlet end 30. In this regard, an initial noncollecting stage 72 is actually positioned between inlet end 28 and the first selection stage 70a. As illustrated in FIG. 3, all of these stages together with body 26 define a fluid flow path from inlet end 28 through the successive stages to outlet 30.

Each of the collection stages thus far described includes an associated fluid jet plate 74 (a, b, c and so on) fixedly located within and extending entirely across the tubular body. Each This fluid jet plate includes a predetermined number of apertures 75 (a, b, c, and so on) each of a predetermined size and shape extending therethrough. Each stage also includes at least one but preferably two impactor collection plates 76 (a, b, c and so on) associated with each plate and located within body 26 adjacent to and downstream of the jet plate. These collector plates include particle collection surfaces in confronting relationship with and a predetermined distance from their associated jet plates. With the exception of the particular design of the apertures (number, size and location) within each jet plate, which design will be discussed hereinafter, the jet plates and their associated collection plates may be identical in operation to the jet plates and collection plates described in the Pilat patent. Hence, a detailed discussion of these plates not be provided herein. However one general difference between the collection stages in the impacter illustrated in FIG. 3 as compared to the impacter illustrated in the Pilat patent (FIG. 3 thereof) resides in the fact that the former includes two paths around each collection plate whereas the latter includes only one such path.

As stated previously, the various stages making up impacter 24 are designed to provide successive pressure drops from one stage to the next. This is actually accomplished by designing the apertures in each plate so as to cause successive drops in pressure between the stages as the fluid moves along its path through the apertures. Moreover, in accordance with the present invention, these apertures in each plate are specifically designed to provide a predetermined ratio of the pressure on its upstream side as compared to the pressure at its downstream side. This predetermined ratio is selected such that the fluid stream flowing through the apertures does so at a rate which does not reach its critical flow rate above which the velocity of fluid through the apertures does not increase with a drop in pressure from the upstream side to the downstream side. To accomplish this in a relatively simple but reliable way, it is only necessary to maintain the ratio between any two stages (with the upstream stage being the numerator and the downstream stage being the denominator) below the Critical Pressure Ratio (for air), that is, less than 1.71 (1/0.585). In this way the flow rate through the various apertures in any given jet plate between two stages will not reach its critical flow rate.

Based on the foregoing, one with ordinary skill in the art could readily determine what the configuration of each jet plate should be in order to meet the criteria set forth above, that is, in order to ensure that the pressure ratio between any two successive upstream and downstream collection stages is below 1.71. In an actual working embodiment of the present invention, impacter 24 has operated in accordance with the pressure data set forth in Table I below. This embodiment used jet plates 74a to 74e (all stainless steel) as shown in FIGS. 4a to 4e. All the dimensions necessary to construct each jet plate including aperture number, size and location are shown. Moreover, FIG. 5 is examplary of the cross-section of each jet plate. It is to be understood that Table I (to follow) and the particular jet plates illustrated are provided for examplary purposes only, as stated. It should be apparent that a given set of jets operates differently at different gas temperatures and, as shown, in some cases, for higher temperatures (at the last stages) may operate above the ratio discussed previously.

Table I

| Gas Temp. (°F.) | Calc. Gas Flow Rate (ACFM) | Downstream Pressures (in.Hg) | | | | | |
|---|---|---|---|---|---|---|---|
| | | Stage 72 | Stage 70a | Stage 70b | Stage 70c | Stage 70d | Stage 70e |
| 100.0 | 1.967 | 29.412 | 27.741 | 24.686 | 21.061 | 14.831 | 8.508 |
| 200.0 | 2.071 | 29.432 | 27.715 | 24.665 | 20.972 | 14.850 | 8.504 |
| 300.0 | 2.126 | 29.455 | 27.812 | 24.699 | 20.852 | 14.941 | 8.504 |

Table I-continued

| Gas Temp. (°F.) | Calc. Gas Flow Rate (ACFM) | Downstream Pressures (in.Hg) | | | | | |
|---|---|---|---|---|---|---|---|
| | | Stage 72 | Stage 70a | Stage 70b | Stage 70c | Stage 70d | Stage 70e |
| 400.0 | 2.161 | 29.474 | 27.942 | 24.731 | 20.719 | 15.029 | 8.499 |
| 500.0 | 2.189 | 29.490 | 28.068 | 24.745 | 20.585 | 15.097 | 8.504 |
| 600.0 | 2.216 | 29.502 | 28.177 | 24.740 | 20.454 | 15.142 | 8.508 |
| 700.0 | 2.245 | 29.511 | 28.269 | 24.719 | 20.327 | 15.162 | 8.499 |
| 800.0 | 2.275 | 29.518 | 28.345 | 24.692 | 20.208 | 15.170 | 8.497 |
| 900.0 | 2.307 | 29.524 | 28.408 | 24.657 | 20.102 | 15.173 | 8.499 |
| 1000.0 | 2.341 | 29.528 | 28.460 | 24.619 | 20.005 | 15.168 | 8.498 |

What is claimed is:

1. An assembly for sampling particleladen fluids for particulate content and particle size distribution, said assembly comprising:
    (a) At least one cascade impactor adapted to be placed within a fluid stream to be sampled, said impactor including
        (i) a longitudinally extending tubular body having a fluid inlet at one end and a fluid outlet at the other end, and
        (ii) a plurality of longitudinally spaced, successive particle collection stages located within said tubular body between said inlet and outlet and, together with said body, defining a fluid flow path from said inlet through successive particle collection stages to said outlet, said stages being constructed and positioned so as to cause successive drops in pressure between said stages as said stream of fluid moves along said path from said inlet to said outlet each of said collection stages including a gas jet plate fixedly located within and extending entirely across said tubular body and having a predetermined number of apertures of predetermined size extending therethrough, and an impactor plate fixedly located within said body adjacent to and downstream of said gas jet plate, said impactor plate including particle collection surface in confronting relationship with and a predetermined distance from said gas jet plate, each of said apertures in any given gas jet plate being designed to provide a ratio of the pressure at its upstream side as compared to the pressure at its downstream side, said ratio being selected below the critical pressure ratio of approximately 1.71 such that the gas stream flowing through said apertures does so at a rate which does not reach its critical flow rate above which the velocity of said fluid through said apertures does not increase with a drop in pressure from said upstream side to said downstream side;
    (b) an arrangement for simulataneously monitoring the pressure at all of said stages, said arrangement including
        (i) a plurality of first means, each of which includes a relatively inflexible tube associated with and having a first end located at and in fluid communication with a corresponding one of said stages for continuously sampling the pressure at that stage during the operation of said assembly, each of said tubes including a second end located in close proximity to its first end,
        (ii) a plurality of second means, each of which is connected with and located in close proximity to the second end of a corresponding one of said tubes and responsive to its continuous sample of pressure for transducing said pressure sample to a corresponding electrical signal,
        (iii) flexible conduit means for carrying said electrical signals from said transducing means to a location remote from said impactor, and
        (iv) third means positioned at said remote location from said impactor, said third means being connected with all of said second means by said flexible conduit means and responsive to said electrical signal for indicating the pressure at each of said stages during operation of said assembly; and
    (c) a control housing positioned at said remote location and including said pressure indicating third means.

2. An assembly according to claim 1 including an arrangement for simultaneously monitoring the temperature at a number of preselected points along said fluid stream including at said inlet and outlet ends of said impactor, said arrangement including:
    (a) an equal number of first means, each of which is located at an associated one of said points for sensing the temperature at that point and producing an electrical signal corresponding thereto during operation of said assembly; and
    (b) means located within said control housing and connected with all of said sensing means for simultaneous indicating the temperature at each of said points in response to said temperature corresponding electrical signals.

3. An assembly according to claim 1 including a second cascade impactor adapted to be placed within said fluid stream upstream of said one cascade impactor, and second impactor including:
    (a) a longitudinally extending tubular body having a fluid inlet at one end and a fluid outlet at the other end, said outlet being interconnected in fluid communication with the inlet of said one impactor,
    (b) a plurality of longitudinally spaced, successive particle collection stages located within its tubular body between its inlet and outlet and, together with its body, defining an upstream fluid flow path from its inlet through successive particle collection stages to its outlet, said last-mentioned stages being constructed and positioned so as to cause substantially no change in pressure between its stage as said stream of fluid moves along said upstream path from its inlet to its outlet.

4. A method of continuously sampling particle-laden fluid from a given stream for particulate content and particle size distribution, said method comprising:
    (a) placing at least one cascade impactor within the fluid stream to be sampled, said impactor including (i) a longitudinally extending tubular body housing a fluid inlet at one end and a fluid outlet at the other end, and (ii) a plurality of longitudinally spaced, successive particle collection stages located within said tubular body between said inlet and outlet and, together with said body defining a fluid flow path from said inlet through successive particle collection stages to said outlet, said stages being constructed and positioned so as to cause successive drops in pressure between said stages as said stream of fluid move along said path from said inlet to said outlet, each of said collection stages including a fluid jet plate fixedly located within and entirely across said tubular body and including a predetermined number of apertures of predetermined size extending therethrough and an impactor plate fixedly located within said body adjacent to and downstream of said jet plate, said impactor plate including a particle collection surface in confronting ralationship with and a predetermied distance from said fluid jet plate, said apertures being provided so as to prevent the flow rate through each of said jet plates from its upstream side to its downstream side from reaching its critical flow rate at which the velocity of said fluid from said upstream side to said downstream side does not increase with a drop in pressure from said upstream side to said downstream side;

(b) continuously sampling simultaneously the pressure at each of said stages during the operation of said assembly, said sampling taking place in its entirely within the confines of said stream, (c) transducing each of said pressure samples to a corresponding electrical signal at a location adjacent the corresponding stage and within the confines of said stream, (d) carrying said electrical signals to a location remote from said impactor and stream, and (e) at a remote location from said impactor and in response to said electrical signals, indicating the pressure at each of said stages.

5. A method according to claim 4 including the step of simultaneously monitoring the temperature at a number of preselected points along said fluid stream including at said inlet and outlet ends of said impactor, said temperature monitoring step including:

(a) sensing the temperature at each of said points and producing an electrical signal corresponding thereto throughout operation of said assembly, (b) at said remote location simultaneously indicating the temperature at each of said points in response to said temperature corresponding electrical signals.

6. A method of sampling particle-laden fluids for particulate content and particle size distribution, said method comprising:

(a) placing at least one cascade impactor within the fluid stream to be sampled, said impactor including (i) a longitudinally extending tubular body having a fluid inlet at one end and fluid outlet at the other end, and (ii) a plurality of longitudinally spaced successive particle collection stages located within said tubular body between said inlet and outlet and, together with said body, defining a fluid flow path from said inlet through successive particle collection stages to said outlet, said stages being constructed and positioned so as to cause successive drops in pressure between said stages as said stream of fluid moves along said path from said inlet to said outlet, each of said collection stages including a fluid jet plate fixedly located within and entirely across said tubular body and including a predetermined number of apertures of predetermined size extending therethrough and an impactor plate fixedly located within said body adjacent to and downstream of said jet plate, said impactor plate including a particle collection surface in confronting relationship with and a predetermined distance from said fluid jet plate; and (b) providing said apertures so as to prevent the rate of flow of said fluid stream from any one of said stages to the next downstream stage from reaching its critical flow rate at which the velocity of said fluid from said one stage to said next downstream stage does not increase with a drop in pressure from said one stage to said next downstream stage.

7. A cascade impactor for use in a train which samples particle-laden fluids for particulate content and particle size distribution, said impactor comprising:

(a) longitudinally extending tubular body having a fluid inlet at one end and a fluid outlet at the other end, (b) a plurality of longitudinally spaced, successive particle collection stages located within said tubular body between said inlet and outlet and together with said body, defining a fluid flow path from said inlet through successive particle collection stages, to said outlet, each of said collection stages including (i) a fluid jet plate fixedly located within and extending entirely across said tubular body for separating that stage from the previous upstream stage, said plate including a predetermined number of apertures each of a predetermined size and shape extending therethrough, and (ii) an impactor plate fixedly located within said body adjacent to and downstream of said jet plate, said impactor plate including a particle collection surface in confronting relationship with and a predetermined distance from said jet plate; and (c) said apertures in each of said plates being of a predesigned number and size (i) so as to cause successive drops in pressure between said stages as said fluid moves along said path from said inlet to said outlet, and (ii) so as to provide a ratio of pressure at its upstream side as compared to the pressure at its downstream side, said ratio being selected to be below the critical pressure ratio of approximately 1.71 such that the fluid stream flowing through said apertures does so at a rate which does not reach its critical flow rate above which the velocity of said fluid through said apertures does not increase with a drop in pressure from said upstream side to said downstream side.

8. A cascade impactor for use in a train which samples particle-laden fluids for particulate content and particle size distribution, said impactor comprising:

(a) a longitudinally extending tubular body having a fluid inlet at one end and a fluid outlet at the other end; and (b) a plurality of longitudinally spaced, successive particle collection stages located within said tubular body between said inlet and outlet and together with said body, defining a fluid flow path from said inlet through successive particle collection stages, to said outlet, said collection stages including means for causing successive drops in pressure between said stages as said fluid moves along said path from said inlet to said outlet, and for providing a ratio of pressure at the upsteam side of each stage as compared to the pressure at its downstream side, said ratio being selected to be below the critical pressure ratios of approximately 1.71 such that the fluid stream flowing through said stages does so at a rate which does not reach its critical flow rate above which the velocity of said fluid through said stages does not increase with a drop in pressure from said upstream side to said downstream side.

* * * * *